(12) United States Patent
Pinney et al.

(10) Patent No.: US 7,123,989 B2
(45) Date of Patent: Oct. 17, 2006

(54) SYSTEM AND METHOD FOR PROVIDING A RANDOM ACCESS AND RANDOM LOAD DISPENSING UNIT

(75) Inventors: Linda J. Pinney, Del Mar, CA (US);
John A. Beane, San Diego, CA (US);
Angus R. Colson, Jamul, CA (US);
David R. Williams, Rainbow, CA (US);
Keith Kopitzke, Fallbrook, CA (US)

(73) Assignee: Asteres, Inc., Del Mar, CA (US)

( * ) Notice: Subject to any disclaimer, the term of this patent is extended or adjusted under 35 U.S.C. 154(b) by 109 days.

(21) Appl. No.: 10/801,321

(22) Filed: Mar. 16, 2004

(65) Prior Publication Data
US 2005/0021173 A1    Jan. 27, 2005

Related U.S. Application Data

(60) Provisional application No. 60/484,544, filed on Jul. 1, 2003.

(51) Int. Cl.
*G06F 17/00* (2006.01)

(52) U.S. Cl. ............... 700/237; 700/216; 700/236; 700/244

(58) Field of Classification Search ........... 700/237, 700/231, 236, 244, 216
See application file for complete search history.

(56) References Cited

U.S. PATENT DOCUMENTS

| | | | |
|---|---|---|---|
| 3,786,421 A | 1/1974 | Wostle et al. | |
| 3,941,977 A | 3/1976 | Voss et al. | |
| 3,943,335 A | 3/1976 | Kinker et al. | |
| 4,359,631 A | 11/1982 | Lockwood et al. | |
| 4,519,522 A | 5/1985 | McElwee | |
| 4,546,901 A | 10/1985 | Buttarazzi | |
| 4,812,629 A | 3/1989 | O'Neil et al. | |
| 4,814,592 A | 3/1989 | Bradt et al. | |
| 4,839,505 A | 6/1989 | Bradt et al. | |
| 4,858,743 A | 8/1989 | Paraskevakos et al. | |
| 4,866,255 A | 9/1989 | Sing | |
| 4,896,024 A | 1/1990 | Morello et al. | |
| 4,951,308 A | 8/1990 | Bishop et al. | |
| 4,995,498 A | 2/1991 | Menke | |
| 5,013,897 A | 5/1991 | Harman et al. | |
| 5,020,958 A | 6/1991 | Tuttobene | |
| 5,036,472 A | 7/1991 | Buckley et al. | |

(Continued)

FOREIGN PATENT DOCUMENTS

WO    WO 02/21402    3/2002

(Continued)

OTHER PUBLICATIONS

Express Scripts company literture; published or in public use at least as early as Jun. 30, 2002; 2 pages.

(Continued)

*Primary Examiner*—Khoi H. Tran
(74) *Attorney, Agent, or Firm*—Heller Ehrman LLP

(57) ABSTRACT

A method of dispensing a prescription drug to a customer includes receiving a prescription for a particular customer from an authorized medical professional, choosing from an inventory of drugs a prescription drug to fill the prescription, creating a finished prescription by filling the prescription with the chosen prescription drug, and placing the finished prescription in a dispenser. The dispenser is connected to a computer, which identifies the finished prescription and controls the dispenser to dispense the finished prescription to the particular customer.

94 Claims, 10 Drawing Sheets

U.S. PATENT DOCUMENTS

| | | |
|---|---|---|
| 5,042,686 A | 8/1991 | Stucki |
| 5,059,772 A | 10/1991 | Younglove |
| 5,088,586 A | 2/1992 | Isobe et al. |
| 5,095,195 A | 3/1992 | Harman et al. |
| 5,105,978 A | 4/1992 | Trouteaud et al. |
| 5,113,351 A | 5/1992 | Bostic |
| 5,139,384 A | 8/1992 | Tuttobene |
| 5,159,560 A | 10/1992 | Newell et al. |
| 5,172,829 A | 12/1992 | Dellicker, Jr. |
| 5,205,436 A | 4/1993 | Savage |
| 5,212,649 A | 5/1993 | Pelletier et al. |
| 5,303,844 A | 4/1994 | Muehlberger |
| 5,313,393 A | 5/1994 | Varley et al. |
| 5,385,265 A | 1/1995 | Schlamp |
| 5,408,443 A | 4/1995 | Weinberger |
| 5,445,294 A | 8/1995 | Gardner et al. |
| 5,445,295 A | 8/1995 | Brown |
| 5,468,110 A | 11/1995 | McDonald et al. |
| 5,482,139 A | 1/1996 | Rivalto |
| 5,499,707 A | 3/1996 | Steury |
| 5,502,944 A | 4/1996 | Kraft et al. |
| 5,593,267 A | 1/1997 | McDonald et al. |
| 5,597,995 A | 1/1997 | Williams et al. |
| 5,713,485 A | 2/1998 | Liff et al. |
| 5,713,487 A | 2/1998 | Coughlin |
| 5,713,648 A | 2/1998 | Geib et al. |
| 5,720,154 A | 2/1998 | Lasher et al. |
| 5,748,485 A | 5/1998 | Christiansen et al. |
| 5,790,409 A | 8/1998 | Fedor et al. |
| 5,797,515 A | 8/1998 | Liff et al. |
| 5,812,410 A | 9/1998 | Lion et al. |
| 5,838,575 A | 11/1998 | Lion |
| 5,839,257 A | 11/1998 | Soderstrom et al. |
| 5,880,443 A | 3/1999 | McDonald et al. |
| 5,893,697 A | 4/1999 | Zini et al. |
| 5,907,493 A | 5/1999 | Boyer et al. |
| 5,930,145 A | 7/1999 | Yuyama et al. |
| 5,945,651 A | 8/1999 | Chorosinski et al. |
| 5,963,453 A | 10/1999 | East |
| 5,971,593 A | 10/1999 | McGrady |
| 6,003,006 A | 12/1999 | Colella et al. |
| 6,021,392 A | 2/2000 | Lester et al. |
| 6,039,251 A | 3/2000 | Holowko et al. |
| 6,068,156 A | 5/2000 | Liff et al. |
| 6,131,399 A | 10/2000 | Hall |
| 6,152,364 A | 11/2000 | Schoonen et al. |
| 6,170,230 B1 | 1/2001 | Chudy et al. |
| 6,199,720 B1 | 3/2001 | Rudick et al. |
| 6,202,923 B1 | 3/2001 | Boyer et al. |
| 6,219,587 B1* | 4/2001 | Ahlin et al. ................ 700/233 |
| 6,230,927 B1 | 5/2001 | Schoonen et al. |
| 6,230,930 B1 | 5/2001 | Sorenson et al. |
| 6,256,967 B1 | 7/2001 | Hebron et al. |
| 6,263,259 B1* | 7/2001 | Bartur ........................ 700/240 |
| 6,283,322 B1 | 9/2001 | Liff et al. |
| 6,305,377 B1 | 10/2001 | Portwood et al. |
| 6,324,520 B1 | 11/2001 | Walker et al. |
| 6,330,491 B1 | 12/2001 | Lion |
| 6,352,200 B1 | 3/2002 | Schoonen et al. |
| 6,354,498 B1 | 3/2002 | Lutz |
| 6,370,841 B1 | 4/2002 | Chudy et al. |
| 6,397,126 B1 | 5/2002 | Nelson |
| 6,397,193 B1 | 5/2002 | Walker et al. |
| 6,416,270 B1 | 7/2002 | Steury et al. |
| 6,438,451 B1 | 8/2002 | Lion |
| 6,443,359 B1 | 9/2002 | Green et al. |
| 6,449,627 B1 | 9/2002 | Baer et al. |
| 6,449,927 B1 | 9/2002 | Hebron et al. |
| 6,464,142 B1 | 10/2002 | Denenberg et al. |
| 6,471,089 B1 | 10/2002 | Liff et al. |
| 6,499,627 B1 | 12/2002 | Arai |
| 6,505,754 B1 | 1/2003 | Kenny et al. |
| 6,522,772 B1 | 2/2003 | Morrison et al. |
| 6,529,801 B1 | 3/2003 | Rosenblum |
| 6,533,170 B1 | 3/2003 | Kit |
| 6,556,889 B1 | 4/2003 | Rudick et al. |
| 6,564,121 B1 | 5/2003 | Wallace et al. |
| 6,581,798 B1 | 6/2003 | Liff et al. |
| 6,584,309 B1 | 6/2003 | Whigham |
| 6,588,548 B1 | 7/2003 | Dewitt |
| 6,594,549 B1 | 7/2003 | Siegel |
| 6,597,970 B1 | 7/2003 | Steury et al. |
| 6,611,810 B1 | 8/2003 | Kolls |
| 6,648,153 B1 | 11/2003 | Holmes |
| 6,697,704 B1 | 2/2004 | Rosenblum |
| 6,766,218 B1 | 7/2004 | Rosenblum |
| 6,814,255 B1* | 11/2004 | Liff et al. ..................... 221/13 |
| 6,874,684 B1* | 4/2005 | Denenberg et al. ......... 235/381 |
| 6,877,655 B1* | 4/2005 | Robertson et al. .......... 235/375 |
| 6,892,941 B1* | 5/2005 | Rosenblum ................. 235/383 |
| 2002/0139810 A1 | 10/2002 | Yuyama et al. |
| 2003/0029882 A1 | 2/2003 | Yuyama et al. |
| 2004/0113786 A1 | 6/2004 | Maloney |
| 2004/0164146 A1 | 8/2004 | Rosenblum |
| 2004/0215369 A1 | 10/2004 | Rosenblum |
| 2005/0049746 A1 | 3/2005 | Rosenblum |

FOREIGN PATENT DOCUMENTS

| | | |
|---|---|---|
| WO | WO 2004/021289 | 3/2004 |

OTHER PUBLICATIONS

Foundation Systems Automated Prescription Point-of-Delivery Kiosk System product literature; published or in public use at least as early as Jun. 30, 2002; 1 page.

Mendota Healthcare, Inc. Business Plan; Dec. 1, 2001; 36 pages.

Mendota Healthcare, Inc. Executive Summary; copyright 2001; 7 pages.

Rowland, Christopher; Drug Vending Units Worry Pharmacists; Jul. 3, 2004; 3 pages.

Declaration of Walter Bain including Exhibit A; executed Sep. 2004; 6 pages.

Declartion of Daniel Bain; executed Sep. 2004; 2 pages.

Letter from Daniel T. Jones; dated May 15, 2001; 1 page.

"Time to switch drugstores?", Consumer Reports, Oct. 2003, 5 pgs.

"Docs try ATM-style prescription machines", CNN.com, Nov. 17, 2001, 2 pgs.

"Vending Pharmacy- Is the long-distance dispensing of drugs the remedy for patients in remote areas?", Drugtopics.com, Mar. 6, 2000, 3 pgs.

"Chains, independents make some gains in technology", Drugtopics.com, Dec. 10, 2001, 3 pgs.

Fleming, Harris, Jr., "Orderly Process—Can central prescription filling help solve pharmacy's time crunch? McKesson thinks it can", Drugtopics.com, Mar. 1, 1999, 3 pgs.

Mendota Healthcare, Inc.'s profile of "InstyMeds" available at www.instymed.com/video.html, 12 pgs.

Jackman, Michael, "Study says chain drug stores ripe for kiosks", KioskMarketPlace.com, Aug. 1, 2001, 2 pgs.

Kieser, Joe, "Medication available at punch of a button", Sun Newspapers, Oct. 31, 2001, 2 pgs.

Mentroy, Jill S., MD, FACS, "Telepharmacy: VA Pharmacy finds Convenience in Vending Machines", Veterans Health System Journal (VHSJ), Oct. 6, 1998, 2 pgs.

Pickpoint Corporation's profile of "FlexCall product" available at http:ww.pickpoint.com/prodcuts-flexcall.html, 23 pgs.

Telepharmacy Solutions, Inc. profile of "TSI's ADDS (Automated Drug Distribution System) product" available at http://www.telepharmacysolutions.com/, 44 pgs.

Ukens, Carol, "Remote Control—Automation puts retail R.Ph.'s foot in doctor's door", Drugtopics.com, Jan. 20, 1997, 1997, 3 pgs.

Ukens, Carol, "Another automated dispenser hits community pharmacy", Drugtopics.com, Sep. 15, 1997, 1997, 3 pgs.

Ukens, Carol, "Pharmacist Shortage Boosts Telepharmacy", Telepharmacy Solutions Media Coverage, Jun. 3, 2002, 2 pgs.

Ukens, Carol, "Technology—Rx vending machine targets pharmacy", Drugtopics.com, Dec. 10, 2001, 3 pgs.

K. Barker et al, "White Paper on Automation In Pharmacy", The Consultant Pharmacists, vol. 13, No. 13, Mar. 1998, pp. 21-37.

McKesson APS: Automated Will Call Rotary Cabinet, available at http://www.mckessonaps.com/wt/aps/prodserv_profiles_willcall.

R. Lewis et al, "Developing The Infrastructure For Patient Care", The Patient-Centered Pharmacy, APhA, 2002, pp. 66-94.

CBS News, "Automated Medicine", Nov. 13, 2001, available at http://www.cbsnews.com/storeis/2001/11/13/health/printable317894.shtml.

PYXIS HELPMATE® SP product literature; published or in public use at least as early as Jun. 30, 2002; 2 pgs.

PYXIS MEDSTATION® 2000 product literature; published or in public use at least as early as Jun. 30, 2002; 1 pg.

PYXIS MEDSTATION®3000 product literature; published or in public use at least as early as Jun. 30, 2002; 1 pg.

PYXIS SUPPLYSTATION® product literature; published or in public use at least as early as Jun. 30, 2002; 4 pgs.

SCRIPTPRO® Pharmacy Automation SP 100 ™ Robotic Prescription Dispensing System product literature; published or in publich use at least as early as Jun. 30, 2002; 2 pgs.

SCRIPTPO® Pharmacy Automation SP 200® Robotic Prescription Dispensing System product literature; published or in publich use at least as early as Jun. 30, 2002; 2 pgs.

SCRIPTPRO® Pharmacy Automation SP Central® Pharmacy Dispensing Managment System product literature; published or in public use at least as early as Jun. 30, 2002; 1 pg.

SCRIPTPRO® Pharmacy Automation SP Station® product literature; published or in public use as least as early as Jun. 30, 2002; 2 pgs.

SCRIPTPRO® Pharmacy Automation SP Automation Center™ (SPace™) product literature; published or in public use at least as early as Jun. 30, 2002; 2 pgs.

SCRIPTPRO® Pharmacy Automation SP Unit Dispenser® (SPUD®) Robotic Pharmaceutical Dispensing System product literature; published or in public use at least as early s Jun. 30, 2002; 2 pgs.

McKesson ACCU MED™ powered by AUTO LINK™ product literature; published or in public use at least as early as Jun. 30, 2002; 2 pgs.

McKesson ACCU SCRIPT™ Pharmacy Robot product literature; published or in public use at least as early as Jun. 30, 2002; 2 pgs.

McKesson BAKER CASSETTES™ product literature; published or in public use at least as early as Jun. 30,2002; 1 pg.

McKesson BAKER CELLS™ product literature; published or in public use at least as early as Jun. 30, 2002; 1 pg.

McKesson MEDCAROUSEL™ product literature; published or in public us at least as early as June 30,2 002; 2 pgs.

McKesson Automated Will Call product literature; published or in public use at least as early as Jun. 30, 2002; 1 pg.

NCR Instymeds Prescription Medication Dispenser product literature; published or in public use at least as early as Jun. 30, 2002; 8 pgs.

NCR FASTLANE™ The Self-Checkout Solution product literature; published or in public use at least as early as Jun. 30, 2002; 8 pgs.

AUTOMED™ Technologies ADDS (Automatic Drug Dispensing System) product literature; published or in public use at least as early as Jun. 30, 2002; 1 pg.

AUTOMED™ Technologies ATC™ Profile System product literature; published or in public use at least as early as Jun. 30, 2002; 2 pgs.

AUTOMED™ Technologies AUTOMED EFFICIENCY PHARMACY™ product literature; published or in public use at least as early as Jun. 30, 2002; 6 pgs.

AUTOMED™ Technologies FASTFILL™ System product literature; published or in public use at least as early as Jun. 30, 2002; 2 pgs.

AUTOMED® FASTPAK™ 71 System product literature; published or in public use at least as early as Jun. 30, 2002; 2 pgs.

AUTOMED® FASTPAK™ 330 and 520 product literature; published or in public use at least as early as Jun. 30, 2002; 4 pgs.

AUTOMED® FASTPAK™ Tabletop System product literature; published or in public use at least as early as Jun. 30, 2002; 2 pgs.

AUTOMED® Technologies Optifill-II System product literature; published or in public use at least as early as Jun. 30, 2002; 4 pgs.

AUTOMED™ Technologies QUICKFILL product literature; published or in public use at least as early as Jun. 30, 2002; 1 pg.

AUTOMED™ Technologies Quickfill Plus product literature; published or in public use at least as early as Jun. 30, 2002; 1 pg.

AUTOMED EFFICIENCY PHARMACY™ R400 product literature; published or in public use at least as early as Jun. 30, 2002; 2 pgs.

AUTOMED EFFICIENY PHARMACY™ R600 product literature; published or in public use at least as early as Jun. 30, 2002; 2 pgs.

AUTOMED EFFICIENY PHARMACY™ R800 product literature; published or in public use at least as early as Jun. 30, 2002; 2 pgs.

AUTOMED EFFICIENY PHARMACY™ R1000 product literature; published or in public use at least as early as Jun. 30, 2002; 2 pgs.

GSL Solutions Will-Call Storage Systems product literature; published or in public use at least as early as Jun. 30, 2002; 4 pgs.

Innovation Associates PharmASSIST Robotic Dispensing Systems (RDS-1 and RDS-11) product literature; published or in public use at least as early as Jun. 30, 2002; 2 pgs.

Innovation Associates SmartCabinet System product literature; published or in public use at least as early as Jun. 30, 2002; 2 pgs.

MedVantx Point-of-Care Automated Sample System product literature; published or in public use at least as early as Jun. 30, 2002; 1 pg.

Parata Systems Parata RDS product literature; published or in public use at least as early as Jun. 30, 2002; 3 pgs.

PICKPOINT™ FLEXRX™ Pharmacy Dispensing product literature; published or in public use at least as early as Jun. 30, 2002; 1 pg.

Supplementary Search Report for corresponding European Application No. 04756405.9 dated Jun. 22, 2006 (3 pgs.).

* cited by examiner

SYSTEM AND METHOD FOR PROVIDING A RANDOM ACCESS AND RANDOM LOAD DISPENSING UNIT

RELATED APPLICATIONS

This is a non-provisional patent application of U.S. Provisional Patent Application Ser. No. 60/484,544 filed on Jul. 1, 2003, which is incorporated herein by reference.

FIELD OF THE INVENTION

The present invention relates generally to dispensing units for dispensing items to individuals and, more particularly, to automated or computer-controlled dispensing units.

BACKGROUND OF THE INVENTION

The typical pharmaceutical transaction entails a doctor ordering a prescription for a patient, the prescription being delivered to a pharmacy, and the patient/customer picking up the finished prescription from the pharmacy.

The typical transaction requires face-to-face interaction between the patient/customer and an available pharmacist, technician, or clerk in order to receive or pick up the finished or filled prescription. In conventional settings, a customer may be required to wait in line to drop off and/or pick up a finished prescription. Further, when the customer can pick up the prescription may be constrained by the hours that a particular pharmacy is open for business. This may result in lost potential sales to a retail establishment in which a pharmacy is located because the customer may cancel a trip to the retail establishment that they otherwise might have made had the pharmacy been open. This may also result in a delay for the customer to pick up time-sensitive prescriptions. A system that allows a customer to pick up a finished prescription without face-to-face contact with pharmacy staff would be welcomed by customers in need of finished prescriptions and the pharmacies serving them.

SUMMARY OF THE INVENTION

The present invention provides, in one aspect, a method of dispensing a prescription drug to a customer. The method includes a pharmacy receiving a prescription for a particular customer from an authorized medical professional, choosing from an inventory of drugs a prescription drug to fill the prescription, creating a finished prescription by filling the prescription with the chosen prescription drug, and placing the finished prescription in a dispenser. The dispenser is connected to a computer, which may identify the finished prescription and control the dispenser to dispense the finished prescription to the particular customer.

The present invention provides, in another aspect, a method of dispensing a prescription drug to a customer. The method includes receiving a prescription for the customer from an authorized medical professional, selecting an appropriate prescription drug to fill the prescription, filling a container with the appropriate prescription drug, storing the container in an automated storage facility, associating the container with a random location in the automated storage facility utilizing a computer, retrieving the container from the random location in the automated storage facility upon an interaction between the customer and the computer, and the automated storage facility dispensing the container to the customer.

Other features and aspects of the present invention will become apparent to those skilled in the art upon review of the following detailed description, claims, and drawings.

BRIEF DESCRIPTION OF THE DRAWINGS

In the drawings, wherein like reference numerals indicate like parts.

Figure 1:
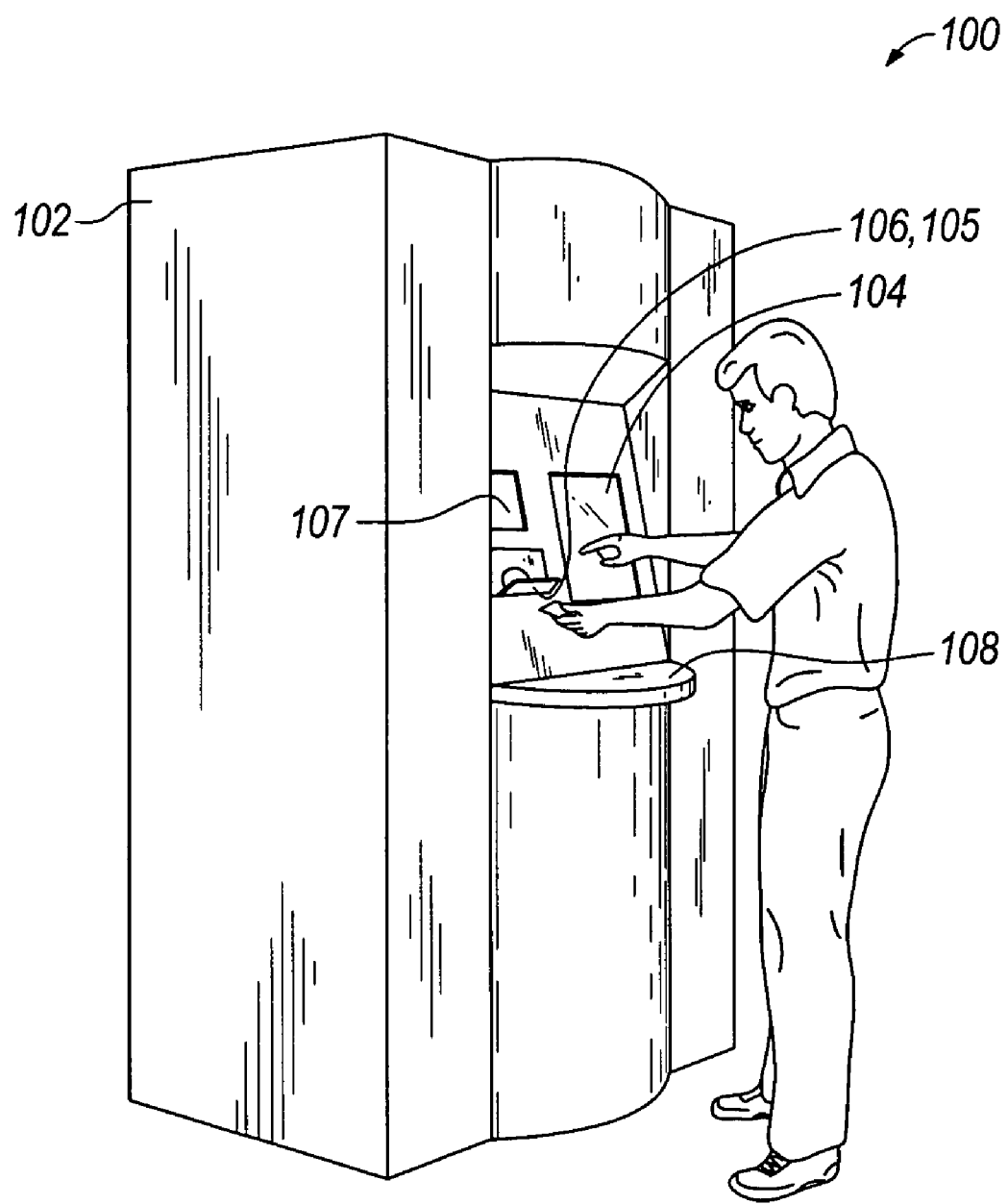
FIG. 1 is a perspective view of a random access and random load dispensing unit of the present invention.

Before any features of the invention are explained in detail, it is to be understood that the invention is not limited in its application to the details of construction and the arrangements of the components set forth in the following description or illustrated in the drawings. The invention is capable of other embodiments and of being practiced or being carried out in various ways. Also, it is understood that the phraseology and terminology used herein is for the purpose of description and should not be regarded as limiting. The use of "including" and "comprising" and variations thereof herein is meant to encompass the items listed thereafter and equivalents thereof as well as additional items. The use of letters to identify elements of a method or process is simply for identification and is not meant to indicate that the elements should be performed in a particular order.

DETAILED DESCRIPTION

FIG. 1 illustrates an automated random-access and random-load dispenser or dispensing unit 100 which allows customers to purchase products, particularly prescription medicines. As shown in FIG. 1, the unit 100 includes a housing 102, means to communicate with the customer (e.g., a touch screen 104, or the like), means to identify the customer (e.g., a magnetic stripe card reader 105), and means to accept payment from the customer (e.g., a cash acceptor or a credit card reader 106). The credit card reader 106 can be utilized as the magnetic stripe card reader 105 to identify the customer. The unit 100 may alternatively or additionally include other identification readers, such as a barcode scanner 107 located at the front of the unit 100. The barcode scanner 107 may work in conjunction with customer identification cards (e.g., drivers licenses, etc.) and/or store cards (e.g., prescription drug cards, pharmacy discount cards, customer loyalty cards, etc.), which typically include a barcode to identify the customer. Further, other identification readers may be utilized, such as fingerprint readers and retinal scanners, for example, to identify the customer.

The touch screen 104 can also be utilized by the customer to initiate customer login. For example, the customer can utilize the touch screen 104 to enter a user name or other identifying information, such as a prescription number. The touch screen 104 can further be utilized by the customer to verify their identity by inputting, for example, a password (e.g., a birth date, social security number, etc.) or a personal identification number. Alternatively, the unit 100 may incorporate more than one touch screen 104, more than one magnetic stripe card reader 105 and/or credit card reader 106, and more than one barcode scanner 107 to allow more than one customer to utilize the unit 100 at a given time.

The unit 100 also includes a computer 124 (see FIG. 4) that is operable to interface with the touch screen 104, the credit card reader 106, and the barcode scanner 107. The computer 124 is shown as a component of the unit 100, but it will be understood by those of ordinary skill in the art that the computer 124 could be remote from the unit 100 and operate the unit 100 through an information connection, such as a network. Further, the computer 124 is shown as dedicated to the unit 100, but multiple units 100 could operate off the same computer 124. The unit 100 would not need its own computer 124, but instead could operate off a computer 124 housed in another unit 100 or not housed within a unit 100 at all. The housing 102 further includes a conveniently located countertop 108 to facilitate the customer's interaction with the unit 100.

Figure 2:
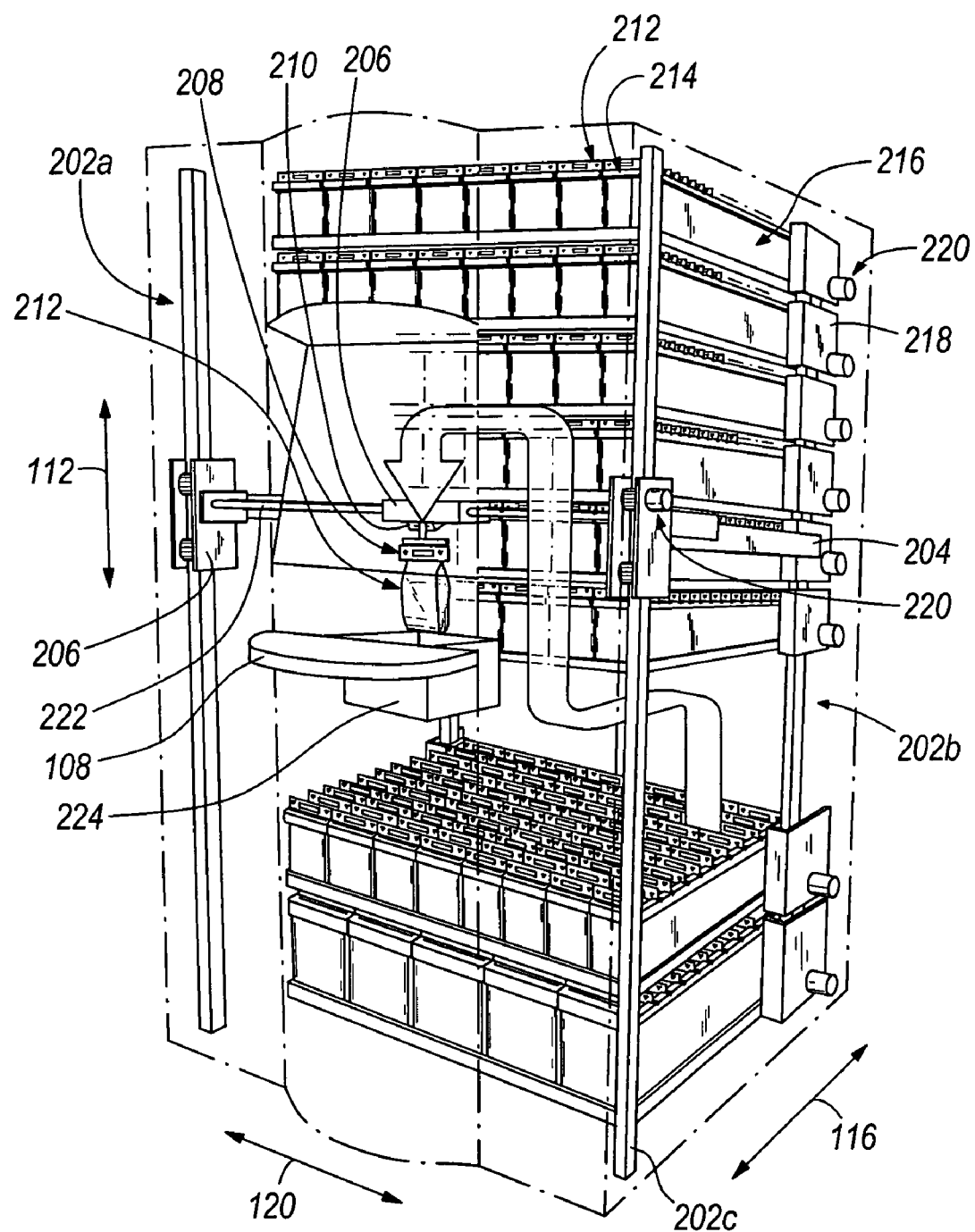
FIG. 2 is a front perspective view of the internal components of the dispensing unit of FIG. 1.
Figure 3:
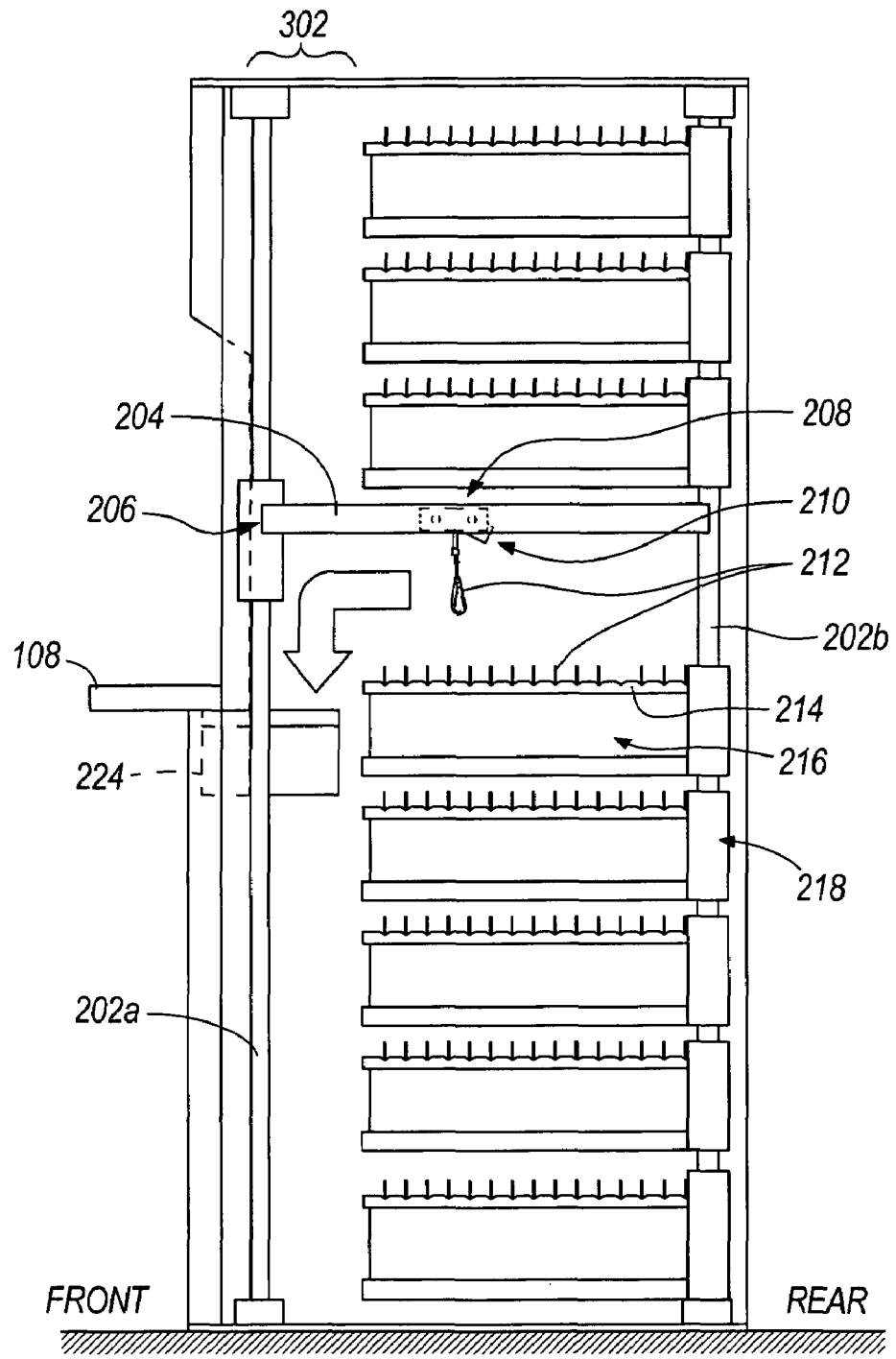
FIG. 3 is a side view of the internal components of the dispensing unit of FIG. 1.
Figure 7:
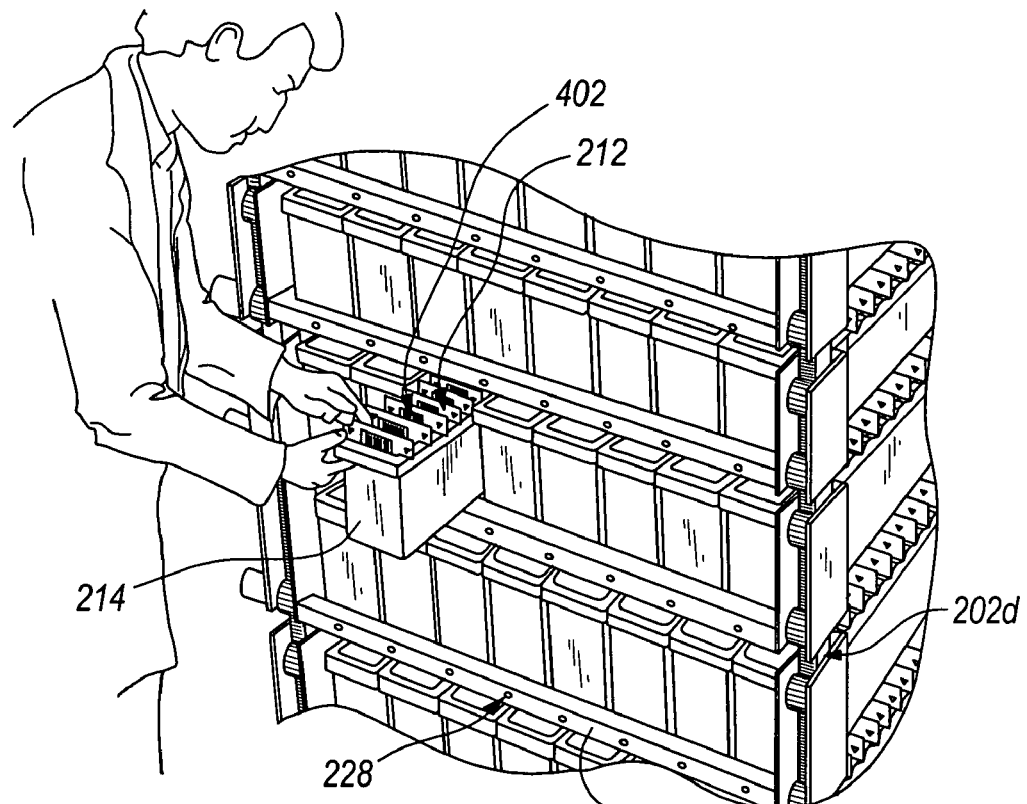
FIG. 7 is a rear perspective view of the dispensing unit of FIG. 1, illustrating the technician loading distribution trays into the dispensing unit.

FIGS. 2 and 3 illustrate the internal components of the unit 100. A plurality of vertically-oriented, or "Y-axis" support members 202a–202d (202d shown in FIG. 7) support a plurality of platforms 216 and a picker assembly 208, such that the platforms 216 and picker assembly 208 are allowed to travel or maneuver along a vertical axis (i.e., Y-axis 112), inside the housing 102. In addition, a "Z-axis" support 204 allows the picker assembly 208 to travel or maneuver from the front of the housing 102 to the rear of the housing 102 (i.e., along Z-axis 116). Further, an "X-axis" support 222 allows the picker assembly 208 to travel or maneuver from side to side in the housing 102 (i.e., along X-axis 120). The Y-axis supports 202a–202d, the Z-axis support 204, and the X-axis support 222 combine to provide a support structure allowing the picker assembly 208 to travel to nearly any location within the housing 102.

Figure 4:
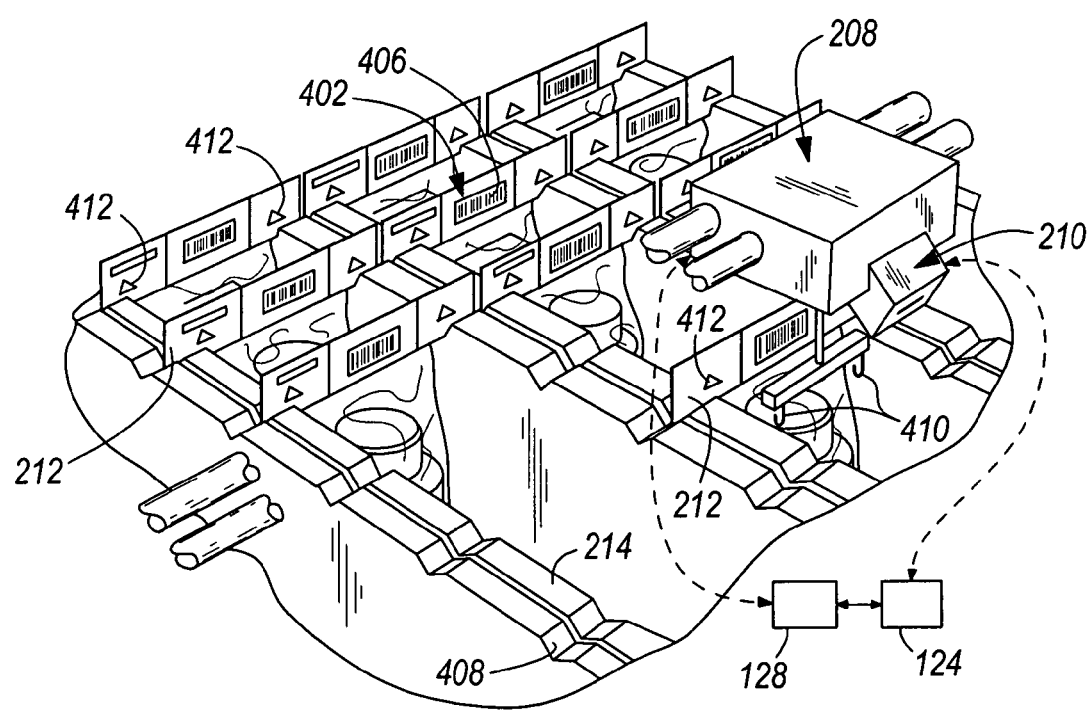
FIG. 4 is a top perspective view of a picker assembly of the dispensing unit of FIG. 1.
Figure 8:
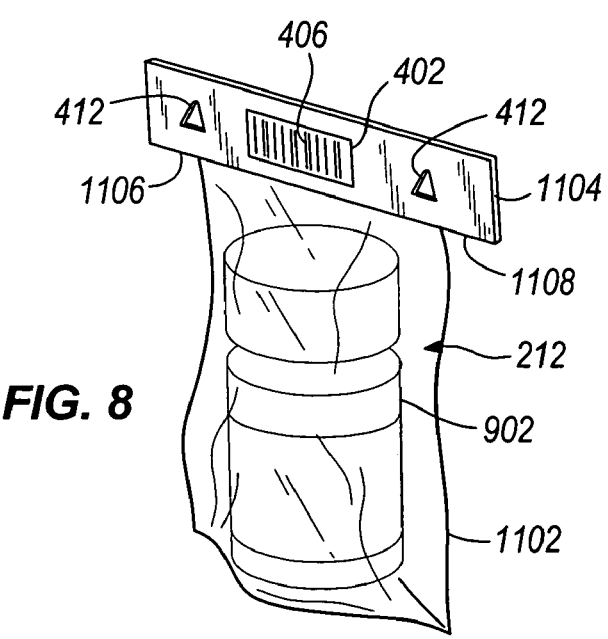
FIG. 8 is a perspective view of a bag or container for storing the finished prescriptions.

As shown in FIG. 4, a plurality of prescription bags 212 are stored in a plurality of distribution trays 214, which, in turn, are supported by the plurality of platforms 216. The prescription bags 212 may include one or more finished prescriptions or containers 902 (see FIG. 8) therein for packaging the prescription drugs. Further, instead of bags 212, other types of containers (e.g., clamshell-type containers) may be stored directly in the trays 214.

The platforms 216 are movable in relation to each other so that a higher density of platforms 216, distribution trays 214, and prescription bags 212 can be stored in the housing 102. Each platform 216 includes means to raise and lower the platform 216 (e.g., gear motor 220), thereby allowing the picker assembly 208 to reach a specific prescription bag 212 stored in a specific distribution tray 214.

With continued reference to FIG. 4, the picker assembly 208 includes a barcode reader 210 for reading barcodes 406 (see FIG. 8) imprinted on the prescription bags 212. In this way, the picker assembly 208 has the capability to associate a specific prescription bag 212 with a random storage location in the housing 102. The barcode reader 210 is operable to interface with the computer 124 to output the locations of the individual bags 212 to a database program in the computer 124. The database program thus provides an inventory of the prescription bags 212 stored in the unit 100. When it is desired to access a selected prescription bag 212, a controller 128 interfaces with the computer 124, the gear motors 220, and the picker assembly 208 to control movement of the platforms 216 and the picker assembly 208 to access the selected prescription bag 212. Although the controller 128 is shown as a separate component from the computer 124, it will be understood by those of ordinary skill in the art that the controller 128 and the computer 124 may be incorporated into a single component.

FIGS. 2 and 3 illustrate the picker assembly 208 delivering a selected prescription bag 212 to a dispense drawer 224 for delivering the prescription bag 212 to a specific customer. As shown in FIG. 2, the selected prescription bag 212 originated from a random slot in a random distribution tray 214 located toward the bottom of the housing 102. Upon identification of the customer, the computer 124 queried the database program to ascertain the location of the selected prescription bag 212. When the location of the prescription bag 212 was determined, the controller 128 interfaced with the lifting mechanism or gear motors 220 to raise the top six platforms 216 to allow access to the distribution tray 214 containing the selected prescription bag 212. The controller 128 then interfaced with the picker assembly 208 to maneuver the picker assembly 208 in place to select the prescription bag 212. Alternatively, more than one picker assembly 208 may be used in the unit 100 to expedite retrieving more than one prescription bag 212.

To dispense the selected prescription bag 212, the picker assembly 208 is advanced toward the front of the housing 102 along the Z-axis, raised along the Y-axis to a position above the distribution tray 214, then moved along the X-axis to position the prescription bag 212 directly above the dispense drawer 224. The picker assembly 208 then releases the prescription bag 212 to drop the prescription bag 212 into the dispense drawer 224. The customer may then open the dispense drawer 224 to pick up the prescription bag 212. Alternatively, more than one dispense drawer 224 or pickup location may be incorporated into the unit 100 if it is desired to service more than one customer at a given time. Further, additional picker assemblies 208 may be incorporated into the unit 100 to service the additional customers.

With reference to FIG. 3, a staging area 302 toward the front of the housing 102 is shown. The staging area 302 allows a working space for the picker assembly 208 to be positioned or stored while the platforms 216 are being moved in anticipation of accessing a particular prescription bag 212. In addition, the staging area 302 provides the working area in which the picker assembly 208 delivers the selected prescription bag 212 to the dispense drawer 224.

FIG. 4 illustrates a close-up view of the picker assembly 208 reading, identifying, and selecting a particular prescription bag 212 from a particular distribution tray 214. The picker assembly 208 utilizes its barcode reader 210 to read a label 402 (also see FIG. 8) that is located on the prescription bag 212. The label 402 includes indicia identifying the contents of the prescription bag 212 and the customer for which the bag 212 is meant. The label 402 is also imprinted with the barcode 406 that is scanned by the barcode reader 210. Alternatively, an electronic identification tag containing information relevant to the customer and/or the prescription may be applied to the prescription bag 212. Accordingly, a reader configured to read the electronic identification tag may be used in place of the barcode reader 210.

The prescription bag 212 may include labels 402 on each side of the bag 212, such that the barcode reader 210 may read the barcode 406 to identify the bag 212 from either side of the bag 212 by reference or query of the database. The distribution trays 214 include self-aligning V-notches 408 so that the label 402 of each bag is accurately positioned in the distribution tray 214 to facilitate reading of the barcodes 406 by the barcode reader 210.

As shown in FIG. 4, the picker assembly 208 includes a mechanism (e.g., hooks 410) for engaging corresponding openings or apertures 412 in the prescription bag 212 to remove the prescription bag 212 from the tray 214. The hooks 410 may be maneuvered to disengage the apertures 412 in the prescription bag 212 when the prescription bag 212 is to be dropped into the dispense drawer 224. Alternatively, the picker assembly 208 may utilize different means for selecting the prescription bags 212, such as, for example, suction, magnets, grabbers, holders, and so forth. As such, the prescription bags 212 may incorporate corresponding structure or features, depending upon the different means for selecting the prescription bags 212, to allow accurate and precise picking of the prescription bags 212.

Figure 5:
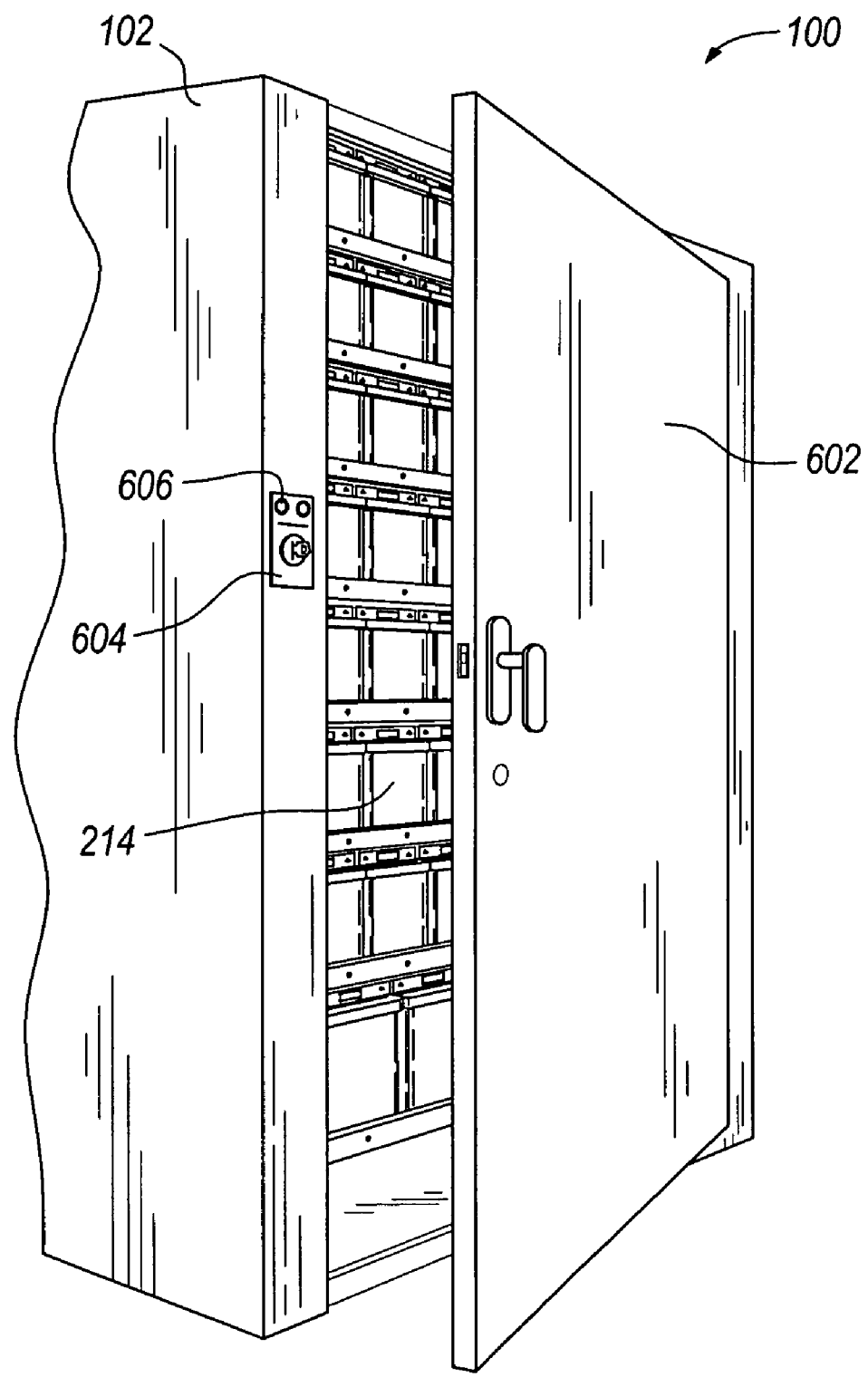
FIG. 5 is a rear perspective view of the dispensing unit of FIG. 1, illustrating a plurality of distribution trays.

FIG. 5 illustrates the rear of housing 102, which is accessed when the unit 100 is to be reloaded with additional prescription bags 212. The housing 102 includes a rear door 602, which may be locked by electronic or mechanical locks 604. The rear of the housing 102 may further include means to communicate with the technician or system operator to display whether the system is prepared to be accessed and reloaded. For example, lights 606 may be provided to communicate with the technician or operator, such as a red light may indicate that the machine is in operation and for the operator to wait to open the rear door 602 or to pull out distribution trays 214. Further, a green light may signal to the technician or operator that the rear door 602 may be opened and that distribution trays 214 may be removed from the unit 100 to be reloaded or inventoried. When the unit 100 is idle, all of the platforms 216 may be moved to their lowest positions in the housing 102 so that bags 212 may not be removed from the distribution trays 214 without a distribution tray 214 being pulled out of the housing 102.

Figure 6:
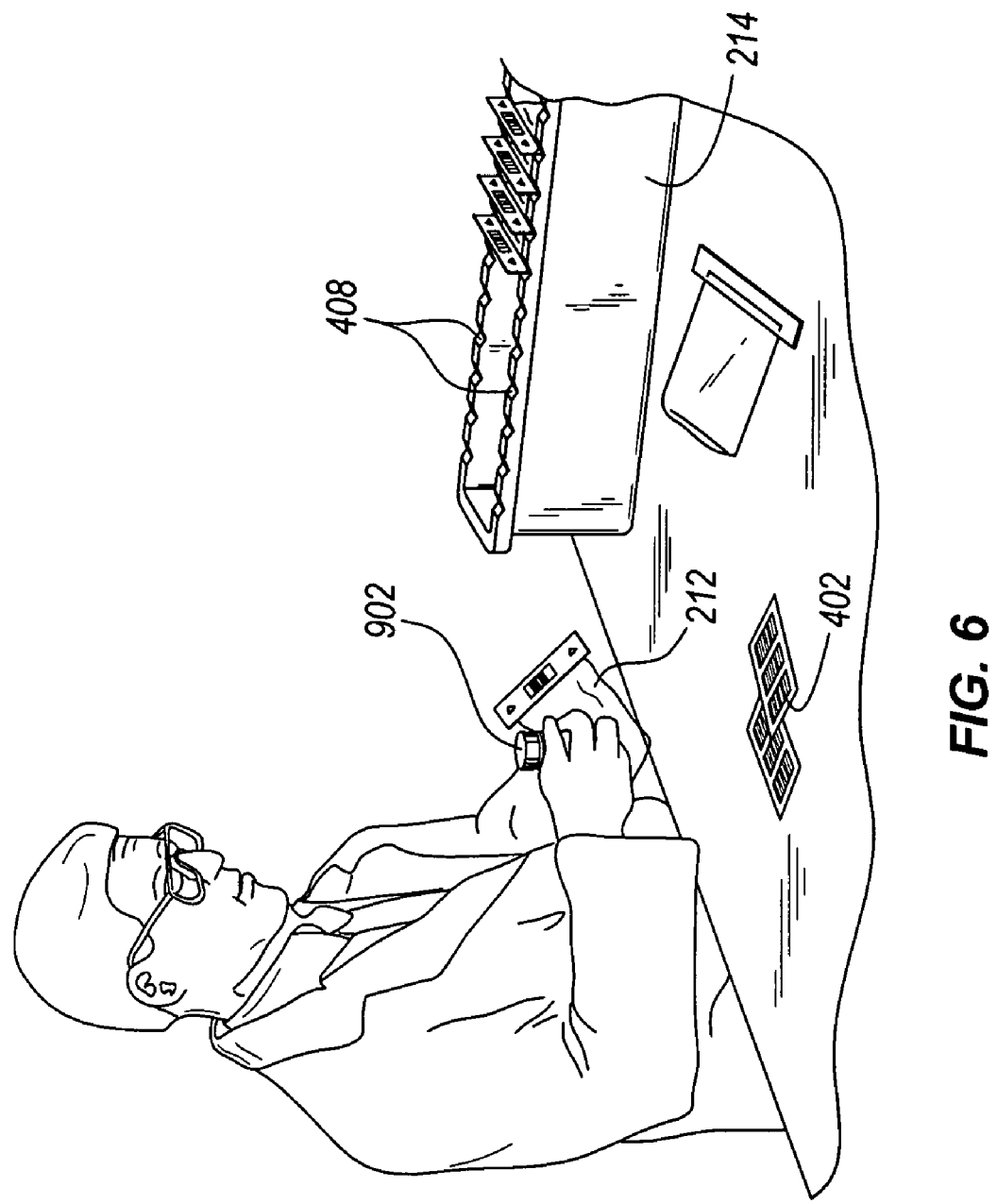
FIG. 6 is a perspective view of a technician/pharmacist loading the distribution trays with finished prescriptions.
Figure 10:
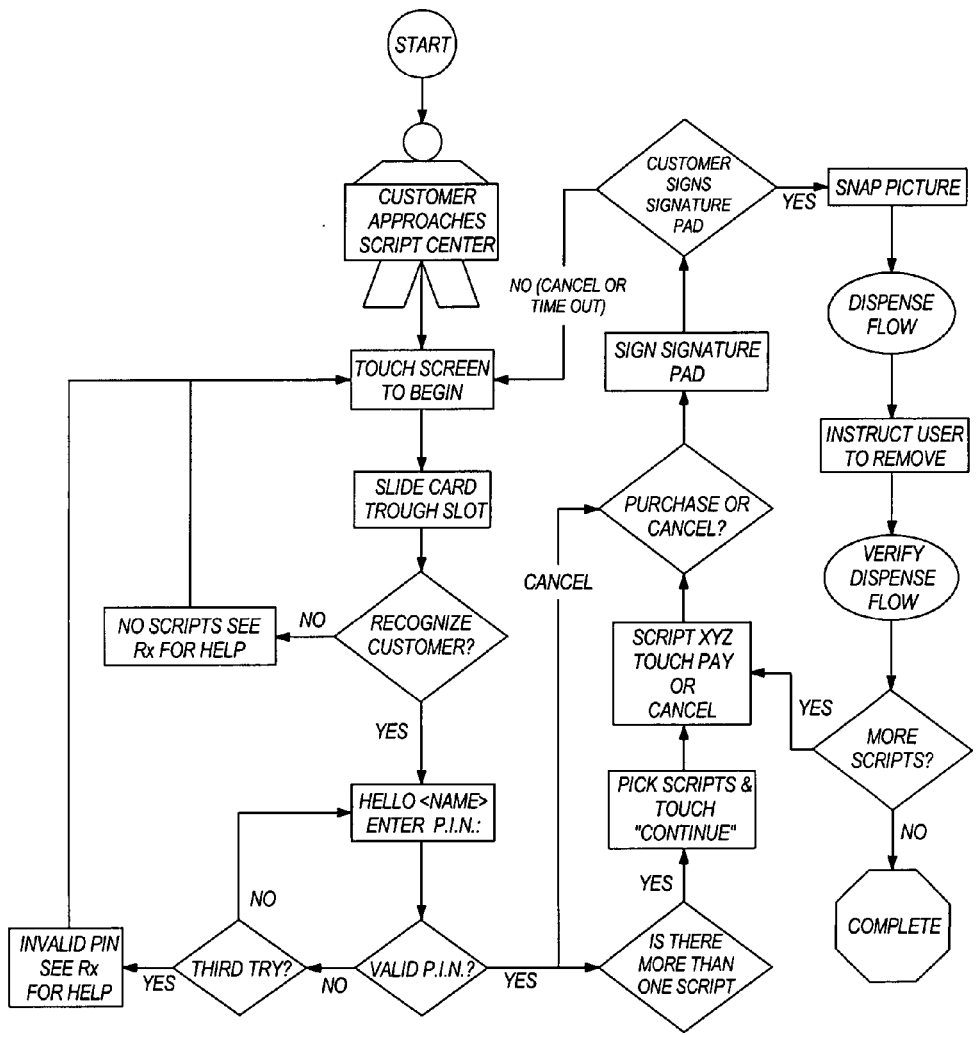
FIG. 10 is a flowchart schematically illustrating the dispensing process of the dispensing unit of FIG. 1.

FIG. 6 illustrates a pharmacist or technician filling prescriptions by placing a prescribed item 902 into the prescription bag 212. The label 402 (including the barcode 406) is placed on the bag 212, and then the bag 212 placed in any random location in the distribution tray 214 so that the bag 212 is captured between the pair of opposing notches 408. With reference to FIG. 10, the pharmacist or technician accesses the rear of the housing 102 via the rear door 602 and places the filled distribution tray 214 into an open slot. The pharmacist or technician may repeat this process as many times as necessary to place new prescription bags 212 into the unit 100 or to fill empty slots in the distribution trays 214.

Figure 9:
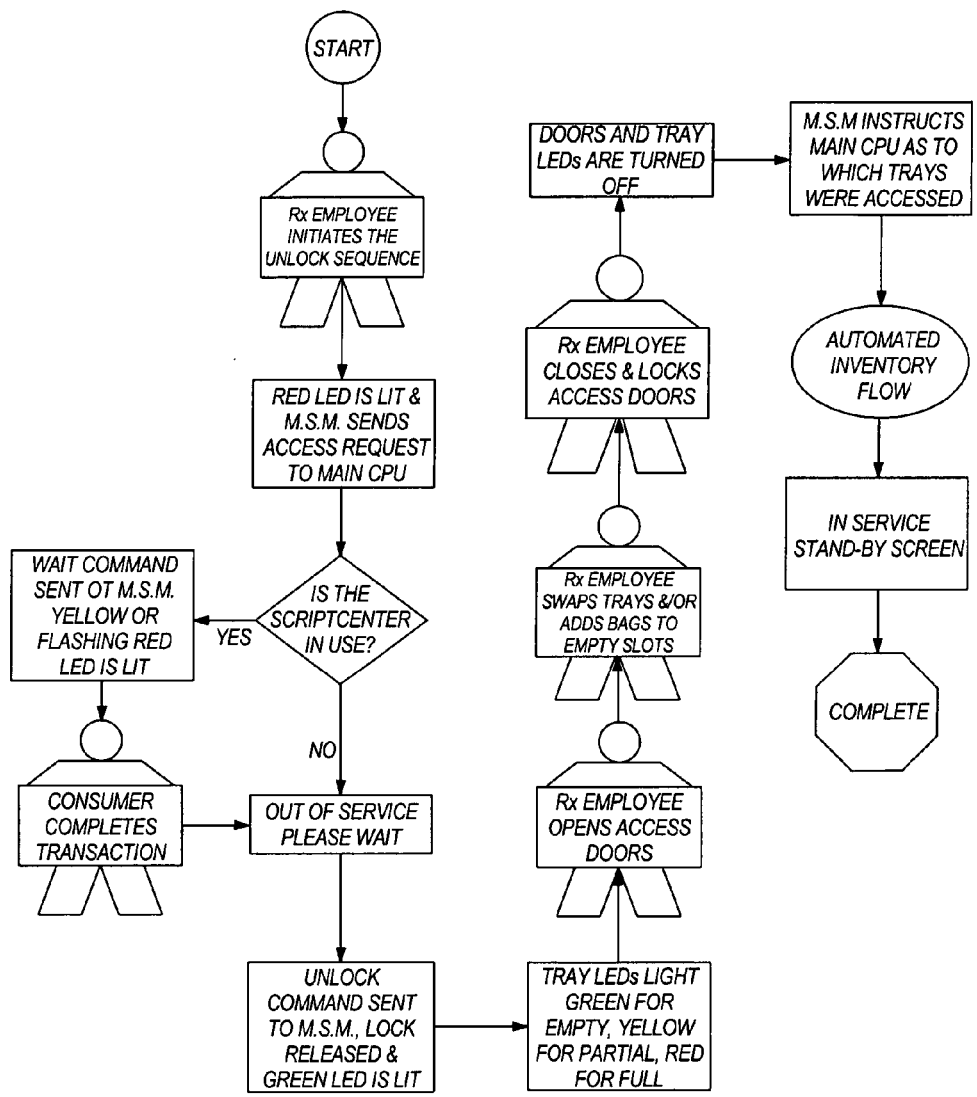
FIG. 9 is a flowchart schematically illustrating the loading process of the dispensing unit of FIG. 1.

With reference to FIG. 9, a process for loading the unit 100 is schematically illustrated. The loading process allows a pharmacist or a technician to replace empty trays 214 with filled trays 214 and/or fill empty slots in partially-empty trays 214 with new prescription bags 212 containing finished prescriptions.

In creating a finished prescription, as is customary, the pharmacist first receives a prescription for a customer from an authorized medical professional, selects an appropriate prescription drug to fill the customer's prescription, and then fills the container 902 with the selected prescription drug to fill the prescription. The pharmacist may then insert the container 902 into the prescription bag 212 and either transfer a label 402 including a barcode 406 from the prescription documentation to the bag 212 to identify the contents of the container 902 and/or the bag 212, or use a barcode reader to scan a pre-printed barcode on the bag 212 and then scan the barcode 406 associated with that prescription to correlate a particular bag 212 to a particular prescription in the database program of the computer 124. The pharmacist or technician may then insert the prescription bags 212 into one or more trays 214 for deposit into the unit 100, or the prescription bags 212 may be deposited into empty slots in partially-empty trays 214 during the loading process.

To load the unit 100, the pharmacist or technician may first initiate a sequence for unlocking the rear door 602. During the sequence to unlock the rear door 602, the controller 128 may interface with the computer 124 to request permission to unlock the rear door 602. If the unit 100 is not in use by a customer, the touch screen 104 may display a message indicating the unit 100 is out of service, and the controller 128 receives a signal from the computer 124 to unlock the rear door 602. After the rear door 602 is unlocked, the pharmacist or technician may visually identify empty trays 214 and replace any empty trays 214 with filled trays 214 containing new prescription bags 212. The trays 214 may be removed and/or replaced in random locations in the unit 100. In other words, the trays 214 are not associated with permanent locations in the unit 100. The pharmacist or technician may also identify which trays are partially empty so that new prescription bags 212 may be inserted in the empty slots in the partially empty trays 214. The pharmacist or technician may identify which trays 214 are empty or partially empty by referencing indicator lights 228 (see FIG. 7) located adjacent the trays 214. The indicator lights 228 (e.g., bi-color LED's) may be varied between different colors and/or intensities (i.e., flashing) by the computer 124 and/or controller 128 to indicate various tray states (e.g., a full tray 214, an empty tray 214, or a partially-empty tray 214).

After the new prescription bags 212 have been deposited into the unit 100, the pharmacist or technician closes and locks the rear door 602. The controller 128 may then interface with the computer 124 to relay which trays 214 were accessed by the pharmacist or technician in order to update the database program in the computer 124 to ascertain an accurate inventory of the prescription bags 212 in the unit 100. The updated inventory of prescription bags 212 in the unit 100 is performed by the picker assembly 208 passing over the new prescription bags 212 and reading their barcodes 406 with the barcode reader 210. To complete the loading process, the computer 124 may prompt the touch screen 104 to display a message indicating the unit 100 is back in service.

With reference to FIG. 10, a process for dispensing the prescription bags 212 is schematically illustrated. The dispensing process may be initiated by a customer touching the touch screen 104, which may display a greeting message to the customer. Then, the customer may be instructed to identify themselves by, for example, sliding their credit card through an identification card reader (e.g., magnetic strip card reader 105 or credit card reader 106). The customer may also have their pharmacy discount card or prescription drug card scanned by the barcode scanner 107 for supplemental or primary identification purposes.

The database program in the computer 124 may then compare the customer's identity with the inventory of prescription bags 212 stored in the unit 100. If a prescription bag 212 corresponding to the customer is not found in the unit 100, the computer 124 may prompt the touch screen 104 to display a message referring the customer to the pharmacist or the technician for assistance. If a prescription bag 212 corresponding to the customer is found in the unit 100, the computer 124 may prompt the touch screen 104 to display a message displaying the customer's name and requesting the customer enter a password to verify their identity. Such a password may include a user-chosen password or a pre-assigned PIN that is stored locally in the database program of the computer 124 or remotely on another database program. If the customer enters an incorrect password or PIN, they may be re-directed back to the password-entry message one or more times before the computer 124 prompts the touch screen 104 to display a message instructing the customer of their invalid password or PIN. From this message, the computer 124 may prompt the touch screen 104 to return to the greeting message at the beginning of the dispensing process.

If the customer enters a password or PIN that is verified by the computer 124, the computer 124 may then query the database program to check the number of prescription bags 212 corresponding to the customer that are stored in the unit 100. The computer 124 may then prompt the touch screen 104 to display a message listing all of the prescription bags 212 corresponding to the customer that are stored in the unit 100. The customer may choose to purchase a first prescription bag 212 by selecting the first prescription bag 212 on the touch screen 104, or the customer may choose to return to the previous message listing all of their prescription bags 212 in the unit 100. Alternatively, if the customer logged in to the unit 100 utilizing the touch screen 104 rather than the credit card reader 106, the customer will be prompted through a payment selection process after selecting their prescription bag 212. Such a payment selection process can include being prompted to enter a credit card into the credit card reader 106 or entering cash into the cash acceptor.

If the customer chooses to continue with the transaction, the computer 124 may prompt the touch screen 104 to display a message instructing the customer to sign their name on a signature pad (not shown) to finalize their purchase of the first prescription bag 212. The customer's signature is recorded electronically by the computer 124. If the customer chooses not to sign the signature pad, the computer 124 may prompt the touch screen 104 to return to the greeting message at the beginning of the dispensing process. However, if the customer signs the signature pad, the computer 124 may prompt a security camera to photograph the customer to produce a photographic record of the transaction.

Figure 11:
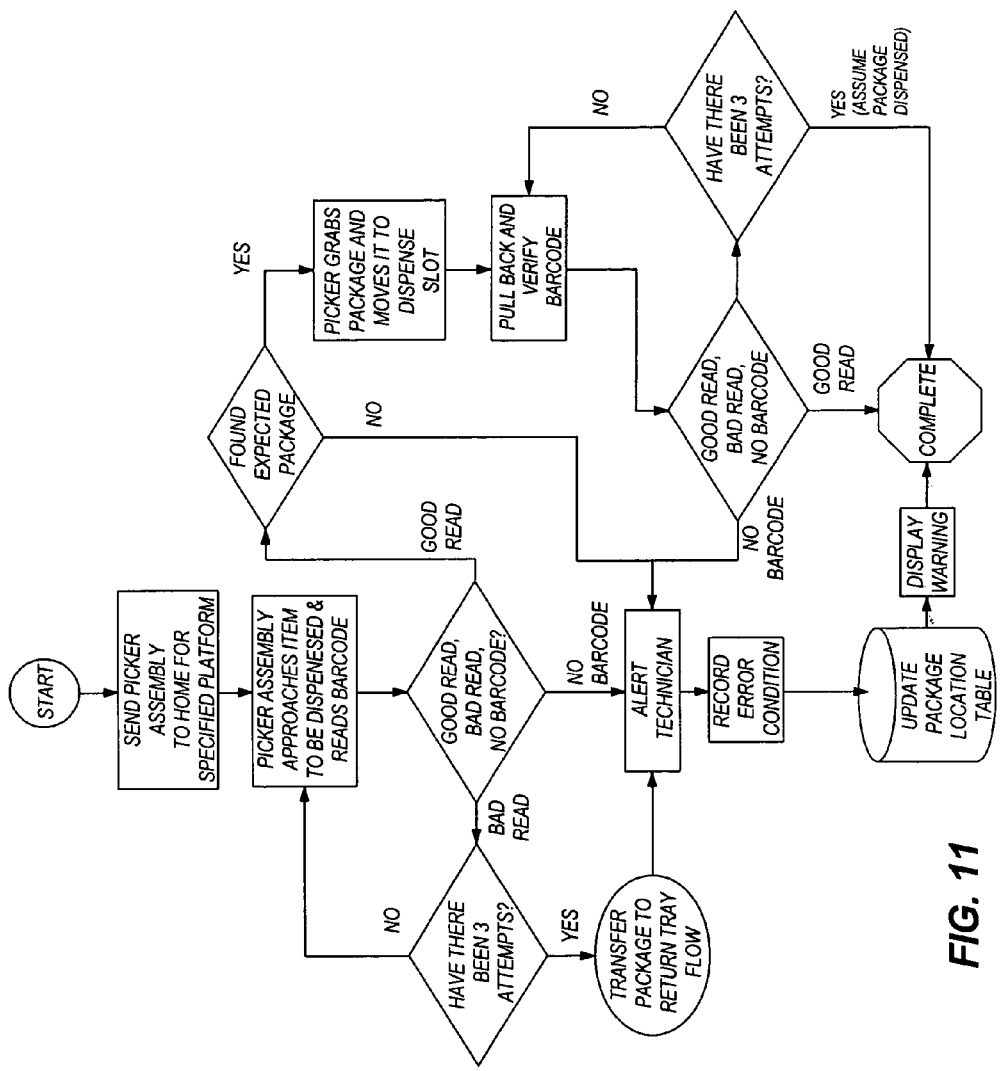
FIG. 11 is a flowchart schematically illustrating the operations performed by the dispensing unit of FIG. 1 in dispensing a finished prescription.

After taking the photograph, the computer 124 may interface with the controller 128 to provide instructions relating the location of the customer's first prescription bag 212. Further, the picker assembly 208 and the platforms 216 may be maneuvered as described above and in the flowchart illustrated in FIG. 11. After the first prescription bag 212 is dispensed into the dispense drawer 224, the computer 124 may prompt the touch screen 104 to display a message instructing the customer to remove the first prescription bag 212 from the dispense drawer 224. The computer 124 may then interface with the controller 128 and/or other sensors or components in the unit 100 to verify the dispensing of the prescription bag 212 and/or the recovery of the prescription bag 212 from the dispense drawer 224.

After dispensing the first prescription bag 212, and if the customer has additional prescription bags 212 stored in the unit 100, the computer 124 may prompt the touch screen 106 to return to the message listing all of the customer's prescription bags 212 stored in the unit 100. The customer may purchase a second prescription bag 212 by repeating the above procedure. If the customer does not have additional prescription bags 212 stored in the unit 100, the transaction may be completed.

The unit 100 may be utilized at a location inside of a store, such as adjacent to a pharmacy counter, so that customers may effectively select, purchase, and receive their prescription drugs, or other consumer items effectively without human interaction in the store. More particularly, customers may purchase their prescription drugs without direct contact with the pharmacist or technician responsible for filing the customer's prescription. In such a capacity, the unit 100 effectively functions as an automated storage facility for storing prescription bags 212 in a location accessible to the customer, even during times when the store or pharmacy is closed. In addition, the unit 100 may be utilized outside of a store location, such as in an automobile drive-through system so that the customer may purchase their prescription bags 212 or other goods while remaining in their automobile.

Although the invention has been described in detail with reference to certain preferred embodiments, variations and modifications exist within the scope and spirit of the invention as described and defined in the following claims.

We claim:

1. A method of dispensing a prescription drug to a customer, the method comprising:
   identifying a particular customer's prescription to fill, said prescription authorized by a medical professional;
   choosing from an inventory of drugs a prescription drug to fill the prescription;
   creating a finished prescription by filling the particular customer's prescription with the chosen prescription drug;
   associating the drug with the particular customer;
   placing the finished prescription in a random location within a computer controlled dispenser;
   automatically associating the finished prescription with a random location in the dispenser after the finished prescription is placed in the dispenser; and
   identifying the finished prescription and controlling the dispenser to dispense the finished prescription to the particular customer upon demand.

2. The method of claim 1, wherein controlling the dispenser comprises translating the finished prescription from the random location to a dispense point in the dispenser.

3. The method of claim 1, further comprising identifying the customer utilizing an identification reader.

4. The method of claim 3, wherein utilizing an identification reader comprises utilizing a magnetic stripe card reader.

5. The method of claim 3, wherein utilizing an identification reader comprises utilizing a reader selected from a group consisting of a fingerprint reader, a retinal scanner, a credit card reader, and a barcode reader.

6. The method of claim 3, further comprising verifying an identity of the customer utilizing a password.

7. The method of claim 1, further comprising: identifying the customer utilizing a user identifying information.

8. The method of claim 7, wherein the user identifying information is selected from a group consisting of a user name, a password, a prescription number, a birth date, a social security number, and a personal identification number.

9. The method of claim 1, further comprising electronically recording a signature of the customer to purchase the finished prescription.

10. The method of claim 1, further comprising photographing the customer during interaction with the dispenser.

11. The method of claim 1, further comprising utilizing the computer to maneuver a picker assembly throughout the dispenser, and wherein the picker assembly dispenses the finished prescription to the customer.

12. The method of claim 1, further comprising verifying the dispensing of the finished prescription.

13. The method of claim 1, further comprising labeling the finished prescription with at least one of a barcode and an electronic identification tag correlating the customer to the finished prescription.

14. The method of claim 1, further comprising utilizing the computer to maneuver a picker assembly throughout the automated storage facility, and wherein the picker assembly dispenses the container to the customer.

15. A method of delivering a customer-specific, pharmacy-filled prescription to a customer comprising:
providing an automated prescription dispenser, said dispenser comprising a computer, a controller, and a three-dimensional array of unique storage locations, each storage location capable of storing a different, customer-specific, pharmacy-filled prescription;
randomly placing a customer-specific, pharmacy-filled prescription into an available storage location, said customer-specific, pharmacy-filled prescription coupled with identifying information associating the prescription with a specific customer;
using said identifying information to associate the randomly-placed, customer-specific, pharmacy-filled prescription with an unique storage location within the dispenser;
controlling the dispenser to locate and deliver the customer-specific, pharmacy-filled prescription from its random storage location after said customer has interfaced with the dispenser and requested delivery.

16. The method of claim 15, wherein the pharmacy filled prescription is a prescription that has been filled by a licensed pharmacist.

17. The method of claim 15, wherein said controlling step further comprises retrieving the customer-specific, pharmacy-filled prescription from the random location in the dispenser.

18. The method of claim 15, further comprising identifying the customer utilizing an identification reader.

19. The method of claim 18, wherein utilizing an identification reader comprises utilizing a magnetic stripe card reader.

20. The method of claim 18, wherein utilizing an identification reader comprises utilizing a reader selected from a group consisting of a fingerprint reader, a retinal scanner, a credit card reader, and a barcode reader.

21. The method of claim 18, further comprising verifying an identity of the customer utilizing a password.

22. The method of claim 15, further comprising identifying the customer utilizing an user identifying information.

23. The method of claim 15, wherein the user identifying information is selected from a group consisting of a user name, a password, a prescription number, a birth date, a social security number, and a personal identification number.

24. The method of claim 15, further comprising electronically recording a signature of the customer before delivering the finished prescription.

25. The method of claim 15, further comprising photographing the customer during interaction with the dispenser.

26. The method of claim 15, wherein said dispenser further comprises a retrieving assembly, and said controlling step further comprises the computer causing the retrieving assembly to maneuver throughout the dispenser to locate and deliver the customer-specific, pharmacy-filled prescription to the customer.

27. The method of claim 26, wherein the retrieving assembly is a picker assembly.

28. The method of claim 15, further comprising the step of verifying that the correct pharmacy-filled, customer-specific prescription is delivered to the correct customer.

29. The method of claim 15, wherein the customer-specific, pharmacy-filled prescription is labeled with at least one of a barcode and an electronic identification tag correlating the customer to the pharmacy-filled, customer-specific prescription.

30. The method of claim 29, wherein said label is used to associate said customer-specific, pharmacist filled prescription with said unique storage location.

31. The method of claim 15, further comprising the step of placing said customer-specific, pharmacy-filled prescription into a storage container before placement into the automated dispenser.

32. The method of claim 31, further comprising placing on the container at least one of a barcode and an electronic identification tag correlating the customer to the pharmacy-filled, customer-specific prescription placed therein.

33. The method of claim 31, wherein said container is a bag.

34. The method of claim 33, wherein said dispenser further comprises a picker assembly, and said controlling step further comprises the computer causing the picker assembly to maneuver throughout the dispenser to locate and deliver the container and the pharmacy-filled, customer-specific prescription to the customer.

35. The method of claim 15, wherein a plurality of distribution trays are housed within the dispenser.

36. The method of claim 35, wherein at least one distribution tray is used to house a plurality of unique storage locations.

37. The method of claim 36, wherein at least one of the distribution trays further comprises a plurality of parallel notches defining the unique storage locations.

38. The method of claim 35, wherein at least one distribution tray is removable from said dispenser.

39. The method of claim 35, wherein the customer specific pharmacy-filled prescriptions are placed at least one of the plurality of distribution trays, and then the distribution trays are placed in the dispenser.

40. The method of claim 39, further comprising the step of placing said customer-specific, pharmacy-filled prescription into a storage container before placement into the distribution tray.

41. The method of claim 40, further comprising placing on the storage container at least one of a barcode and an electronic identification tag correlating the customer to the pharmacy-filled, customer-specific prescription placed therein.

42. The method of claim 41, wherein said storage container is a bag.

43. The method of claim 42, wherein said barcode label is placed substantially near the top of the bag.

44. The method of claim 15, wherein said computer is located remotely from said dispenser.

45. The method of claim 15, wherein said dispenser is located in a pharmacy.

46. The method of claim 15, wherein said dispenser is located remotely from a pharmacy.

47. The method of claim 46, further comprising the step of moving a previously stored, customer specific, pharmacy-filled prescription from one unique storage location located within the dispenser to another unique storage location located within the dispenser.

48. The method of claim 15, wherein said pharmacy-filled, customer specific prescription is stored among hundreds of other customer-specific, pharmacy-filled prescriptions within the dispenser.

49. A method of delivering a pharmacy-filled prescription to a customer, wherein the pharmacy-filled prescription is associated with identifying information associating the prescription with a specific customer; the method comprising:
providing an automated prescription dispenser, said dispenser comprising a controller, and a plurality of unique storage locations, a first axis, a second axis, and a third axis, wherein said storage locations are each capable of storing unique, pharmacy-filled prescriptions associated with different specific customers, wherein a plurality of unique storage locations are located in the plane formed by the first axis and the second axis, a second plurality of unique storage locations are located in the plane formed by the first axis and the third axis, and a third plurality of unique storage locations are located in the plane formed by the second axis and the third axis;
placing a customer-specific, pharmacy-filled prescription at a random storage location within the dispenser;
allowing a customer access to the dispenser;
using the specifically associated identifying information to locate the customer-specific, pharmacy-filled prescription stored for the particular customer accessing the dispenser;
controlling the dispenser to deliver the customer-specific, pharmacy-filled prescription from its unique storage location to the accessing customer.

50. The method of claim 49, wherein the pharmacy filled prescription is a prescription that has been filled by a licensed pharmacist.

51. The method of claim 49, wherein said controlling step further comprises retrieving the customer-specific, pharmacy-filled prescription from the random location in the dispenser.

52. The method of claim 49, wherein said storage location is not assigned until after placement in the dispenser.

53. The method of claim 49, further comprising identifying the customer utilizing an identification reader, the identification reader being part of the dispenser.

54. The method of claim 53, wherein utilizing an identification reader comprises utilizing a magnetic stripe card reader.

55. The method of claim 53, wherein utilizing an identification reader comprises utilizing a reader selected from a group consisting of a fingerprint reader, a retinal scanner, a credit card reader, and a barcode reader.

56. The method of claim 53, further comprising verifying an identity of the customer utilizing a password.

57. The method of claim 49, further comprising identifying the customer utilizing an user identifying information.

58. The method of claim 57, wherein the user identifying information is selected from a group consisting of a user name, a password, a prescription number, a birth date, a social security number, and a personal identification number.

59. The method of claim 49, further comprising electronically recording a signature of the customer before delivering the customer-specific, pharmacy-filled prescription.

60. The method of claim 49, further comprising photographing the customer during interaction with the dispenser.

61. The method of claim 49, wherein said dispenser further comprises a translating assembly, and said controlling step further comprises the computer causing the translating assembly to maneuver throughout the dispenser to locate and deliver the customer-specific, pharmacy-filled prescription to the customer.

62. The method of claim 61, wherein the translating assembly is a picker assembly.

63. The method of claim 49, further comprising the step of verifying that the correct customer-specific, pharmacy-filled prescription is delivered to the correct customer.

64. The method of claim 49, wherein the customer-specific, pharmacy-filled prescription is labeled with at least one of a barcode and an electronic identification tag correlating the customer to the customer-specific, pharmacy-filled prescription.

65. The method of claim 64, wherein said label is used to associate said customer-specific, pharmacist filled prescription with said unique storage location.

66. The method of claim 49, further comprising the step of placing said customer-specific, pharmacy-filled prescription into a storage container before placement into the automated dispenser.

67. The method of claim 66, further comprising placing on the storage container at least one of a barcode and an electronic identification tag correlating the customer to the pharmacy-filled, customer-specific prescription placed therein.

68. The method of claim 66, wherein said container is a bag.

69. The method of claim 68, wherein said dispenser further comprises a picker assembly, and said controlling step further comprises the computer causing the picker assembly to maneuver throughout the dispenser to locate and deliver the container and the pharmacy-filled, customer-specific prescription to the customer.

70. The method of claim 49, wherein a plurality of distribution trays are housed within the dispenser.

71. The method of claim 70, wherein at least one of the plurality of distribution trays is used to house a plurality of unique storage locations.

72. The method of claim 70, wherein at least one distribution tray is removable from said dispenser.

73. The method of claim 72, wherein the pharmacy-filled, customer specific prescriptions are placed in the distribution tray, and then the distribution tray is placed in the dispenser.

74. The method of claim 73, wherein at least one of the distribution trays further comprises a plurality of parallel notches defining the unique storage locations.

75. The method of claim 73, further comprising the step of placing said customer-specific, pharmacy-filled prescription into a storage container before placement into the distribution tray.

76. The method of claim 75, further comprising placing on the container at least one of a barcode and an electronic identification tag correlating the customer to the pharmacy-filled, customer-specific prescription placed therein.

77. The method of claim 75, wherein said container is a bag.

78. The method of claim 77, wherein said barcode label is placed substantially near the top of the bag.

79. The method of claim 78, further comprising the step of moving a previously stored, customer specific, pharmacy-filled prescription from one unique storage location located within the dispenser to another unique storage location located within the dispenser.

80. The method of claim 49, wherein said computer is located remotely from said dispenser.

81. The method of claim 49, wherein said dispenser is located in a pharmacy.

82. The method of claim 49 wherein said dispenser is located remotely from a pharmacy.

83. A method of delivering a pharmacy-filled prescription to a customer, wherein the pharmacy-filled prescription is associated with identifying information associating the prescription with a specific customer; the method comprising:
   providing an automated prescription dispenser, said dispenser comprising a computer, controller, and a plurality of unique storage locations, wherein said plurality of unique storage locations are arranged in a three-dimensional array, and said storage locations are each capable of storing unique, pharmacy-filled prescriptions substantially associated with different specific customers;
   placing a customer-specific, pharmacy-filled prescription at a random, unassigned storage location within the dispenser;
   using said identifying information to associate the randomly-placed, customer-specific, pharmacy-filled prescription with an unique storage location within the dispenser;
   allowing a customer access to the dispenser;
   using the specifically associated identifying information to locate the customer-specific, pharmacy-filled prescription stored for the particular customer accessing the dispenser;
   controlling the dispenser to deliver the customer-specific, pharmacy-filled prescription from its unique storage location to the accessing customer.

84. The method of claim 83, wherein the pharmacy filled prescription is a prescription that has been filled by a licensed pharmacist.

85. A method of delivering a customer-specific, pharmacy-filled prescription to a customer comprising:
   providing an automated prescription dispenser, said dispenser comprising a controller and a plurality of bins, each bin capable of storing a different, customer-specific, pharmacy-filled prescription;
   randomly placing a customer-specific, pharmacy-filled prescription substantially into an available bin, said customer-specific, pharmacy-filled prescription containing identifying information associating the prescription with a specific customer;
   associating the randomly-placed, customer-specific, pharmacy-filled prescription with the specific bin location within the dispenser where the customer-specific, pharmacy-filled prescription was placed;
   identifying the randomly stored, customer-specific, pharmacy-filled prescription, after said customer has interfaced with the dispenser and requested delivery;
   controlling the dispenser to deliver the customer-specific, pharmacy-filled prescription from its random storage location to the particular customer.

86. The method of claim 85, wherein the pharmacy filled prescription is a prescription that has been filled by a licensed pharmacist.

87. A method of delivering a customer-specific, pharmacy-filled prescription to a customer comprising:
   providing an automated prescription dispenser, said dispenser comprising a controller and a plurality of trays, each tray capable of storing a plurality of different, customer-specific, pharmacy-filled prescription;
   randomly placing a customer-specific, pharmacy-filled prescription into an available tray, said customer-specific, pharmacy-filled prescription containing identifying information associating the prescription with a specific customer;
   after placement, using said identifying information to associate the customer-specific, pharmacy-filled prescription with a specific tray location within the dispenser;
   identifying the randomly stored, customer-specific, pharmacy-filled prescription, after said customer has interfaced with the dispenser and requested delivery;
   controlling the dispenser to deliver the customer-specific, pharmacy-filled prescription from its random storage location to the particular customer.

88. The method of claim 87, wherein the pharmacy filled prescription is a prescription that has been filled by a licensed pharmacist.

89. The method of claim 87, wherein the tray is removable from the dispenser.

90. The method of claim 89, further comprising the step of placing the customer-specific, pharmacy-filled prescription substantially in the tray while the tray is removed from the dispenser.

91. The method of claim 90, wherein the tray houses a plurality of unique storage locations.

92. The method of claim 91, wherein the unique storage locations are defined by parallel v-shaped notches located on opposite sides of the trays.

93. The method of claim 92, further comprising the step of placing several customer-specific pharmacy-filled prescription substantially in the tray while the tray is removed from the dispenser, and then returning the tray to the dispenser when customer-specific, pharmacist filled prescriptions have been placed at all unique storage locations.

94. The method of claim 93, wherein a tray contains customer-specific, pharmacy-filled prescriptions for different customers.

\* \* \* \* \*